United States Patent
Heinz et al.

(10) Patent No.: US 7,678,114 B2
(45) Date of Patent: Mar. 16, 2010

(54) VERTEBRAL IMPLANT INSERTER AND METHOD OF USE

(75) Inventors: Eric Steven Heinz, Memphis, TN (US); John Stewart Young, Memphis, TN (US)

(73) Assignee: Warsaw Orthopedic, Inc.

( * ) Notice: Subject to any disclaimer, the term of this patent is extended or adjusted under 35 U.S.C. 154(b) by 537 days.

(21) Appl. No.: 11/313,038

(22) Filed: Dec. 20, 2005

(65) Prior Publication Data

US 2007/0161989 A1    Jul. 12, 2007

(51) Int. Cl.
A61F 5/00 (2006.01)
A61B 17/58 (2006.01)

(52) U.S. Cl. .................. 606/86 A; 606/99

(58) Field of Classification Search .......... 606/99, 606/86 A, 276; 623/17.11–17.16
See application file for complete search history.

(56) References Cited

U.S. PATENT DOCUMENTS

| | | | | |
|---|---|---|---|---|
| 3,562,912 A | * | 2/1971 | Edelman | 433/147 |
| 4,347,845 A | * | 9/1982 | Mayfield | 606/86 R |
| 4,411,259 A | * | 10/1983 | Drummond | 606/86 A |
| 4,502,474 A | | 3/1985 | Comparetto | |
| 4,557,259 A | | 12/1985 | Wu | |
| 4,955,885 A | | 9/1990 | Meyers | |
| 5,098,437 A | * | 3/1992 | Kashuba et al. | 606/89 |
| D331,625 S | | 12/1992 | Price et al. | |
| 5,246,442 A | | 9/1993 | Ashman et al. | |
| 5,484,440 A | * | 1/1996 | Allard | 606/916 |
| 5,496,321 A | | 3/1996 | Puno et al. | |
| 5,499,986 A | * | 3/1996 | Dimarco | 606/104 |
| 5,529,494 A | * | 6/1996 | Vlacancich | 433/105 |
| 5,941,885 A | | 8/1999 | Jackson | |
| 6,139,549 A | * | 10/2000 | Keller | 606/86 A |
| 6,174,335 B1 | | 1/2001 | Varieur et al. | |
| 6,692,503 B2 | * | 2/2004 | Foley et al. | 606/96 |
| 6,712,819 B2 | | 3/2004 | Zucherman et al. | |
| 6,764,491 B2 | * | 7/2004 | Frey et al. | 606/85 |
| 6,923,830 B2 | * | 8/2005 | Michelson | 623/17.16 |
| 6,929,647 B2 | | 8/2005 | Cohen | |
| 7,179,261 B2 | * | 2/2007 | Sicvol et al. | 606/86 A |
| 7,226,406 B2 | * | 6/2007 | Muller et al. | 600/25 |
| 2003/0149484 A1 | | 8/2003 | Michelson | |
| 2005/0283244 A1 | * | 12/2005 | Gordon et al. | 623/17.15 |

FOREIGN PATENT DOCUMENTS

WO    9220294 A1    11/1992
WO    2005096968 A1    10/2005

* cited by examiner

*Primary Examiner*—Eduardo C Robert
*Assistant Examiner*—Ellen C Hammond

(57) ABSTRACT

A surgical installation tool to insert a vertebral implant into a patient includes an elongated handle and a head attached to one end. The vertebral implant may be attached to the head. The head may include an engagement member that is movable between engaged and released positions. The engagement member may be outwardly biased so that it naturally rests in the released position. The engagement member may be inwardly movable from the released position to the engaged position. A reactive force caused by the inward deflection may supply the attachment force between the installation tool and the vertebral implant. The attachment between the vertebral implant to the installation tool may be maintained while the engagement member is in the engaged position.

23 Claims, 7 Drawing Sheets

VERTEBRAL IMPLANT INSERTER AND METHOD OF USE

BACKGROUND

Vertebral implants such as spinal hooks are sometimes used in spinal implant systems for the treatment of spinal deformities and fractures. Conditions for which spinal implants may be indicated include degenerative disc disease, vertebral fractures, scoliosis, or other conditions that cause instability of the spine. One type of spinal implant comprises hooks and/or pedicle screws attached to rods on one or each lateral side of the vertebrae. As surgical techniques advance, minimally intrusive procedures requiring smaller incisions are more commonly used to attach spinal implants such as these. As such, the surgical insertion tools that are used to hold and insert the implant components are a part of this improving trend.

Many conventional insertion tools grasp the spinal implant components about the exterior of the component. Further, some conventional insertion tools may not provide an optimal angle of approach for inserting the component, particularly with small surgical incisions. Accordingly, improvements in surgical insertion tools may help advance the trend towards less intrusive surgical procedures.

SUMMARY

Embodiments of a surgical installation tool are disclosed. The installation tool may be used to insert a vertebral implant into a patient. The vertebral implant may be attached to one end of the installation tool. The attachment end of the installation tool may include an engagement member that is movable between engaged and released positions. The engagement member may be outwardly biased so that it naturally rests in the released position. The engagement member may be inwardly movable from the released position to the engaged position. A reactive force caused by the inward deflection may supply the attachment force between the installation tool and the vertebral implant. The attachment between the vertebral implant to the installation tool may be maintained while the engagement member is in the engaged position.

DETAILED DESCRIPTION

Figure 1:
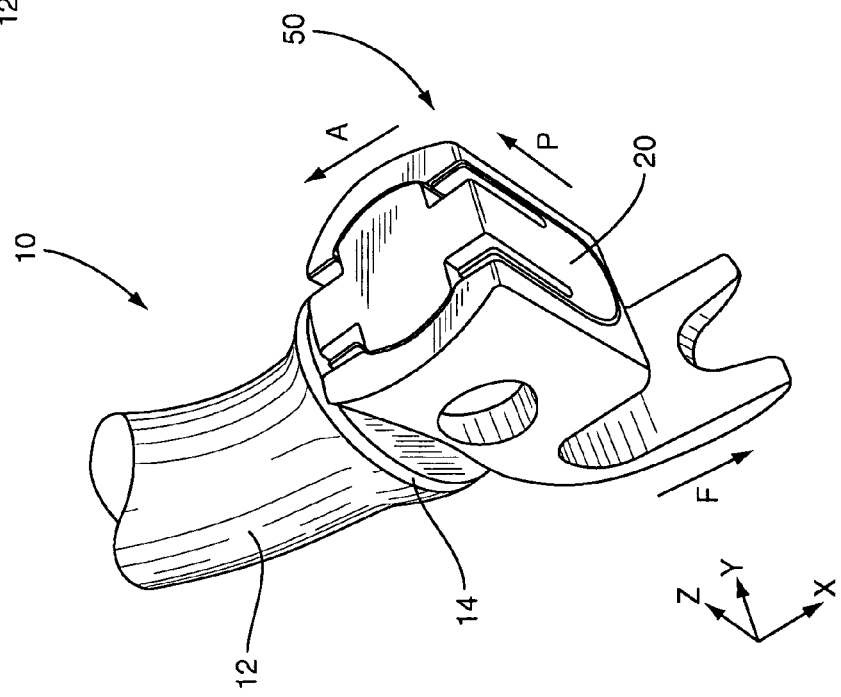
FIG. 1 is a perspective view of an insertion tool holding an implant device according to one embodiment.

The various embodiments disclosed herein are directed to a low profile surgical implant insertion tool. An exemplary embodiment of the insertion tool 10 is illustrated in FIG. 1. In this particular embodiment, the insertion tool 10 is illustrated holding a hook implant 50. The hook 50 may be a conventional distraction hook or other hook implant such as that belonging to the CD HORIZON® LEGACY™ Spinal System available from Medtronic Sofamor Danek in Memphis, Tenn. Various types of hooks may be held and positioned using the insertion tool 10, including for example pedicle hooks, supralaminar hooks, infralaminar hooks, and transverse process hooks.

Figure 2:
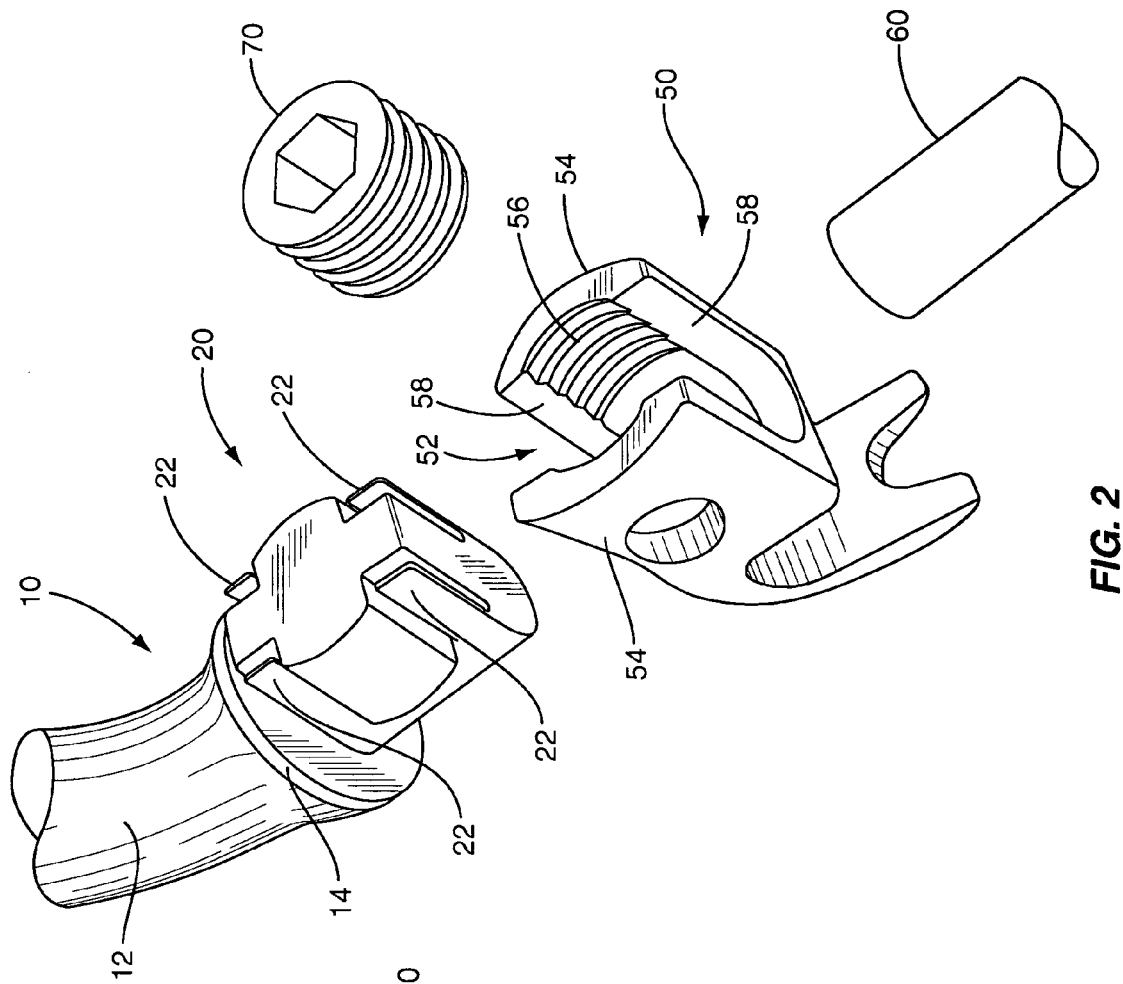
FIG. 2 is an exploded assembly view of an insertion tool and an implant device according to one embodiment.

In FIG. 1, the hook 50 is held by the exemplary insertion tool 10. In contrast, FIG. 2 shows the hook 50 separated from the insertion tool 10. The insertion tool 10 includes an elongated bar 12 having a head or retainer 20 disposed at an end of the elongated bar 12. The insertion tool 10 may be manipulated during surgery by maneuvering the elongated bar 12 to place the hook 50 in a desired position relative to a vertebral member (not shown). The retainer 20 is configured to hold the hook 50 in a releasable manner. Thus, once the hook 50 is positioned, the insertion tool 10 may be extracted, leaving the hook 50 substantially in the desired position.

The retainer 20 is shaped to fill much of the saddle portion 52 of the hook 50. In the embodiment shown, the saddle portion 52 comprises spaced apart side walls 54 having a substantially U-shaped open channel therebetween. It is between these side walls 54 that a spinal rod 60 of a spinal implant system is inserted. In the illustrated embodiment of a hook 50, the side walls 54 include a threaded central portion 56 into which a retaining member 70 is inserted to secure the rod 60 within the saddle portion 52 of the hook 50.

The retainer 20 has a generally U-shaped configuration, which permits insertion of the retainer 20 into the saddle portion 52 of the hook 50. The retainer 20 further comprises a plurality of biasing members 22. In this embodiment, the biasing members 22 are configured as cantilevered leaf springs and operate as engagement elements that contact the hook 50. Furthermore, in the embodiment shown, the retainer 20 has four biasing members 22, though a different number may be used. The insertion tool 10 is configured such that, when the retainer 20 is inserted into the saddle 52 of the hook 50 as shown in FIG. 1, the biasing members 22 frictionally engage inner faces 58 of the side walls 54 on either side of the threaded portion 56. The biasing force applied by the biasing members 22 against the inner side walls 58 of the hook 50 is sufficient to support the weight of the hook 50. However, as suggested above, the retainer 20 and the biasing members 22 hold the hook 50 in a releasable manner. Thus, the biasing members 22 should not create so large a retaining force that the insertion tool 10 cannot be extracted from the hook 50 as needed.

The exemplary insertion tool 10 also includes an enlarged flange 14 adjacent to the retainer 20. The flange 14 serves to limit the depth to which the hook 50 may be inserted onto the retainer 20. In addition, the flange 14 permits the application of an insertion force in the direction indicated by the letter F in FIG. 1. For instance, it may be necessary to apply an insertion force in the direction of arrow F during surgical installation of the hook 50. However, once the hook 50 is positioned as desired, the arrangement of the retainer 20 and flange 14 allow the insertion tool 10 to be removed in the directions indicated by arrow A or arrow P or some vector combination thereof. These arrows F, A, and P are shown relative to an X-Y-Z coordinate system. Note also that the direction of deflection of the biasing members 22 caused by installation of the hook 50 onto the retainer 20 in one or more embodiments may be substantially aligned with the Y-coordinate.

Figure 3A:
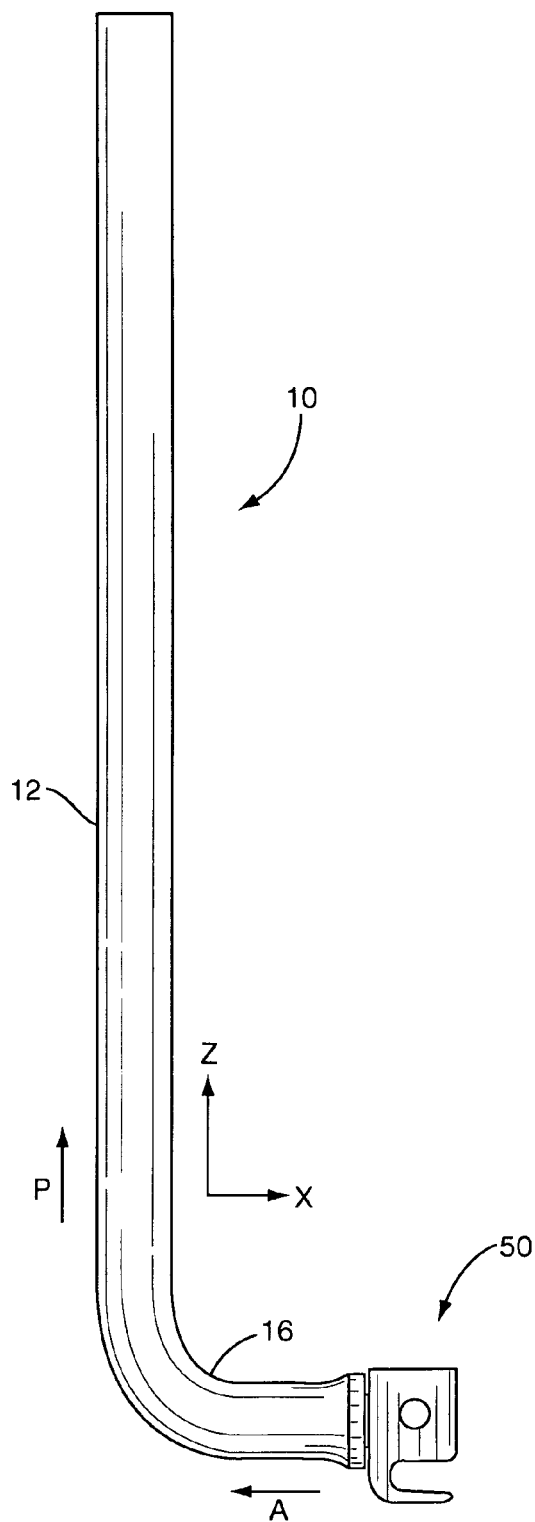
FIGS. 3A-3B are side views of an insertion tool holding an implant device according to one embodiment.

FIG. 3A shows arrows A and P relative to the same X-Y-Z coordinate system and to the entire insertion tool 10 and hook 50. Notably, the elongated bar 12 is substantially aligned with the direction of removal along arrow P. This direction P is towards the open part of the U-shaped channel in the saddle 52 (see FIG. 2). This direction P is also substantially perpendicular to the rod 60 that lies within the U-shaped channel in saddle 52. The ability to remove the insertion tool in this direction may help preserve the desire to maintain small surgical incisions and may also prevent interference with vertebrae or other anatomy (not shown). Furthermore, since the retainer 20 fits substantially within the interior of the saddle 52, the extent to which the insertion tool 10 is a limiting factor in guiding and placing the hook 50 in a desired position may be minimized. Also, the size of the insertion tool 10 in the direction of arrow A may be minimized by adjusting the size of the bend 16 in the elongated bar 12 and the distance between the bend 16 and the distal end at which the hook 50 is attached.

Figure 3B:
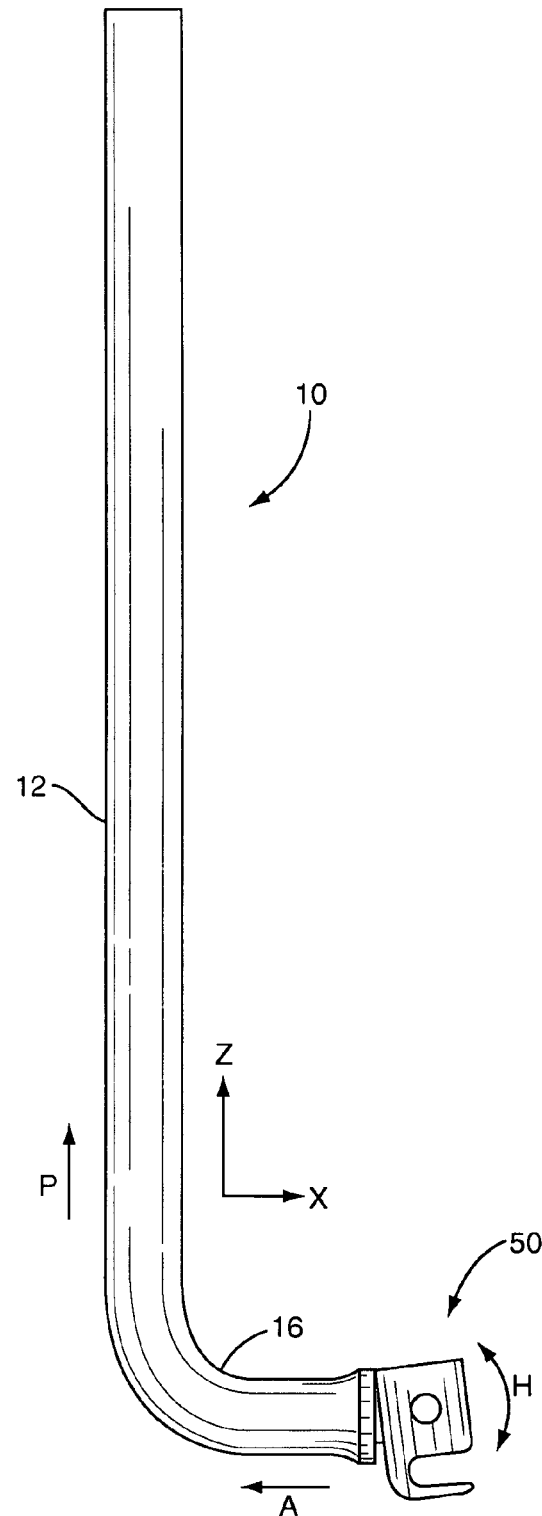

As described above and shown in FIG. 2, the retainer 20 uses friction to grasp the inner surfaces 58 of side walls 54 of the hook 50. Consequently, there is some amount of flexibility in orienting the hook 50 onto the retainer 20. That is, as FIG. 3B shows, the hook 50 may be rotated slightly up and down in the X-Z plane as indicated by the arrows H relative to the insertion tool 10. This additional degree of flexibility may further improve approach angles during surgical installation as well as in removing the insertion tool 10 from the hook 50.

Figure 4:
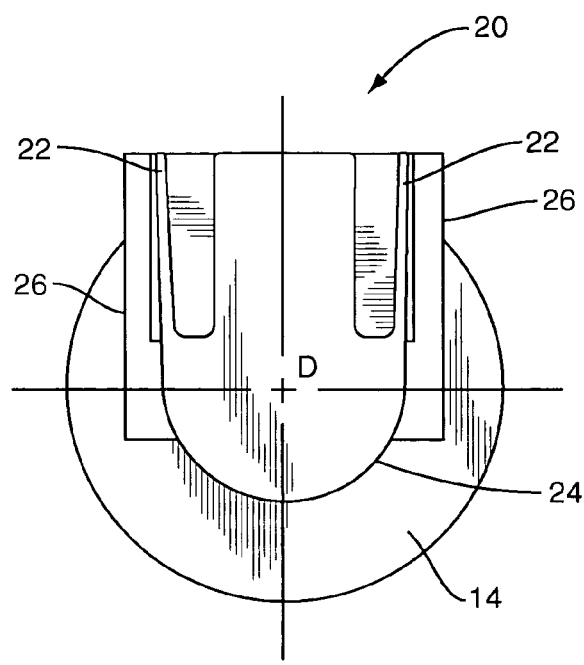
FIG. 4 is a frontal view of a retainer of an insertion tool according to one embodiment.

The U-shaped configuration of the retainer 20 is more clearly visible in the frontal view shown in FIG. 4. This particular view is aligned with a longitudinal axis labeled D. The bottom surface 24 is curved to fit within the saddle 52 of hook 50. In one embodiment, the bottom surface 24 of retainer 20 has a radius of curvature that matches that of the bottom of saddle 52 (see FIG. 2). This same radius of curvature may also correspond to a diameter of rod 60 (also shown in FIG. 2). FIG. 4 also illustrates a small outward bow of the biasing members 22 relative to the width of the bottom surface 24. The biasing members 22 are resilient and deflect inward, conforming to the size of the saddle 52 of hook 50 (as shown in FIG. 1). The reaction force caused by this inward deflection supplies the friction that holds the hook 50 onto the retainer 20.

Figure 5:
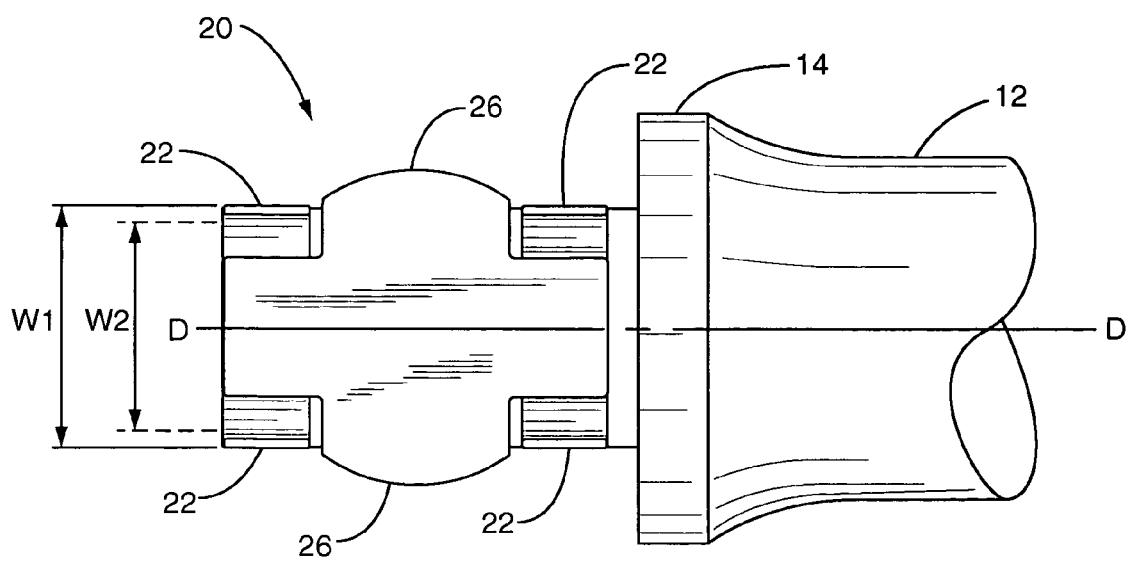
FIG. 5 is a top view of a retainer of an insertion tool according to one embodiment.

FIG. 5 shows a top view of the exemplary retainer 20, including the biasing members 22, in relation to the flange 14 and elongated bar 12. Notably, the middle portion 26 between the biasing members 22 extends wider than the biasing members 22 (also visible in FIG. 3). When the retainer 20 is inserted into the saddle 52 of the hook 50 as shown in FIG. 1, these middle portions 26 fit within the threaded portion 56 of the hook 50. A close fit between the middle portions 26 of retainer 20 and the threaded portions 56 of hook 50 may contribute to a more robust retention, reducing unwanted motion between the two parts 10, 50. A widened middle portion 26 may omitted in cases where the hook 50 or other vertebral implant does not have the threaded portions 56.

FIG. 5 also shows that the retainer 20 is oriented along the longitudinal axis labeled D. The biasing members 22 are positioned in a free state and are spaced apart a first width W1 in a direction substantially perpendicular to the longitudinal axis D. When the hook 50 is attached as illustrated in FIG. 1, the biasing members 22 deflect inward towards an engaged state where the biasing members are space apart a second width illustrated by the dimension labeled W2. This inward deflection of the biasing members 22 creates the outward retention force that keeps the hook 50 attached to the retainer 20. Note that the length of the retainer in the left to right direction of FIG. 5 remains substantially constant.

Figure 7:
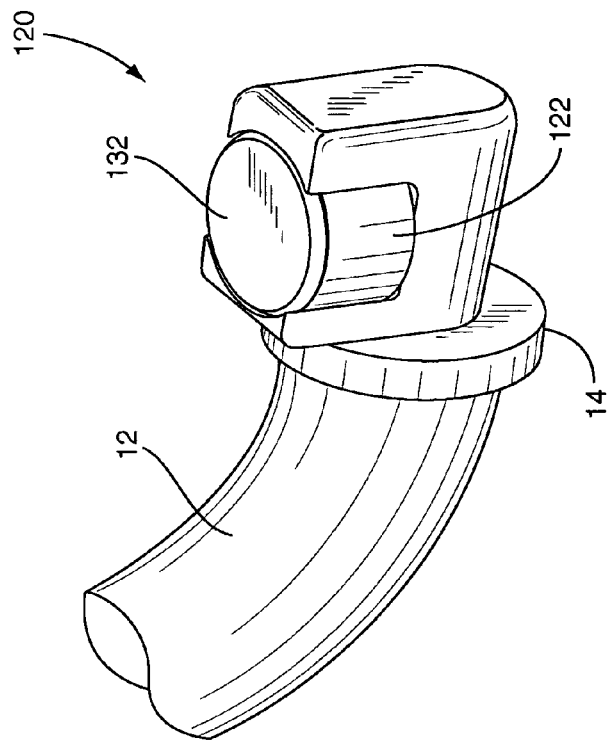
FIG. 7 is a perspective view of an insertion tool according to one embodiment.
Figure 6:
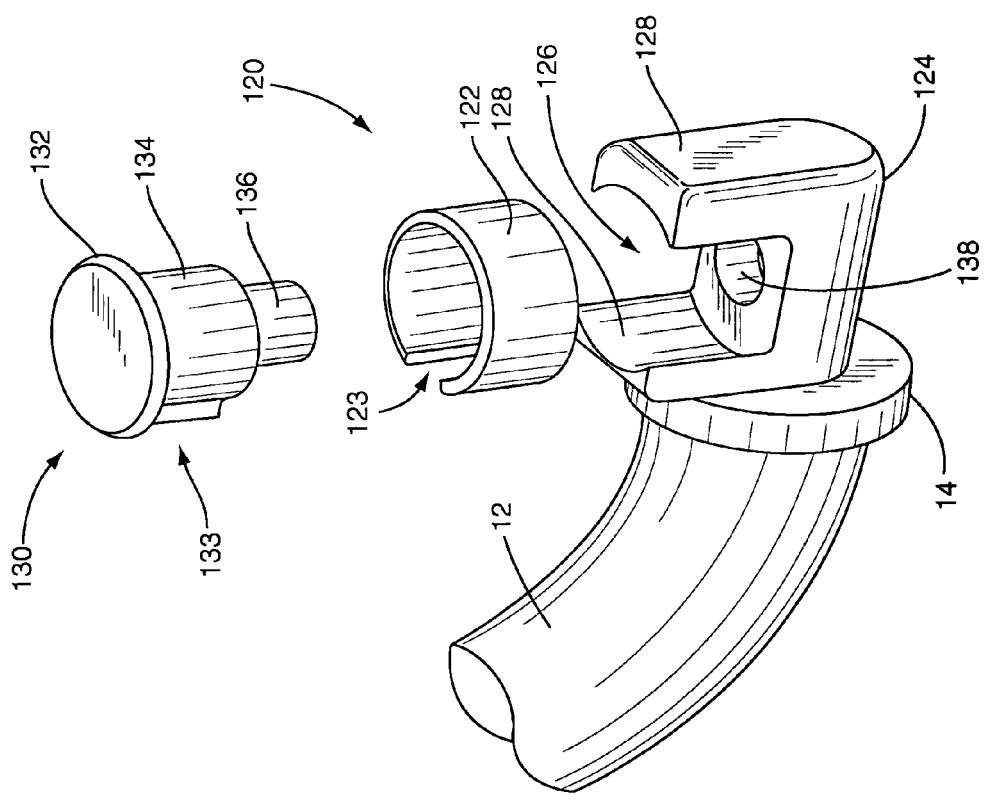
FIG. 6 is an exploded assembly view of an insertion tool according to one embodiment.

An alternative embodiment of a retainer 120 is illustrated in FIGS. 6-9. FIG. 6 shows an exploded view of components in this particular embodiment. The retainer 120 uses a biasing member 122 to apply a retaining force to a hook 50. In the embodiment shown, the biasing member 122 is a compression ring. The biasing member 122 fits within a recess 126 formed between retaining walls 128 of a substantially U-shaped retainer body 124 protruding from flange 14. In one embodiment, this retainer body 124 is sized to fit within the saddle 52 of the hook 50 shown in FIG. 2. The biasing member 123 is captured within the recess 126 by a substantially cylindrical plug 130. The plug 130 includes three portions 132, 134, 136 defined by different diameters. A flange portion 132 has a diameter that is larger than the inner diameter of the biasing member 122. The body portion 134 has a diameter that is smaller than the inner diameter of the biasing member 122. Further, a plug portion 136 has a diameter that is sized to fit within a corresponding aperture 138 in the retainer body 124. The plug portion 136 may be threaded to fit within a corresponding threaded aperture 138. Alternatively, the plug portion 136 may be press fitted into the aperture 138. In other embodiments, the plug portion 136 may be loosely fit into aperture 138, but retained using an adhesive compound. As configured, the plug 130 may retain the biasing member 122 as shown in FIG. 7.

The biasing member 122 further comprises a gap 123 that is larger than a corresponding orienting feature 133 in the body portion 134 of the plug 130. This relationship among these features is more readily visible in FIG. 8, which shows a top view of the exemplary retainer 120. The gap 123 in biasing member 122 is aligned with the orienting feature 133. The gap 123 is wider than the orienting feature 133 as evidenced by the existence of gaps 123 on either side of the orienting feature 133. Also as indicated, the body portion 134 (see FIG. 6) has a diameter that is smaller than the biasing member 122. This difference in size allows resilient compression of the biasing member 122 in the direction indicated by the arrows labeled C in FIG. 8, which is substantially perpendicular to the longitudinal axis D.

Figure 8:
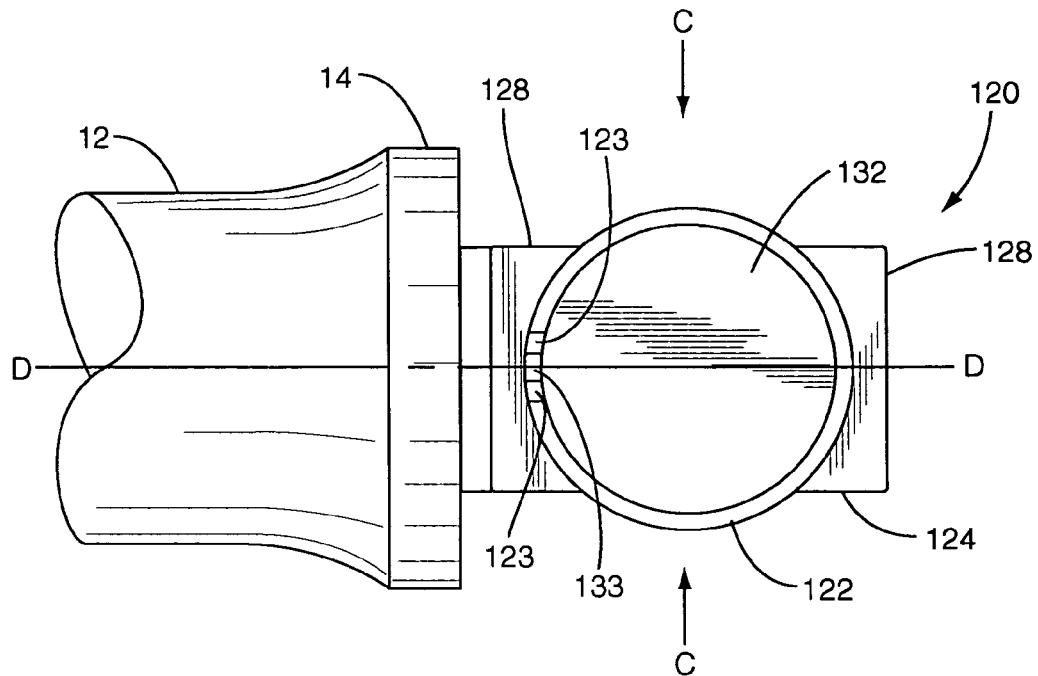
FIG. 8 is a top view of a retainer of an insertion tool according to one embodiment.
Figure 9:
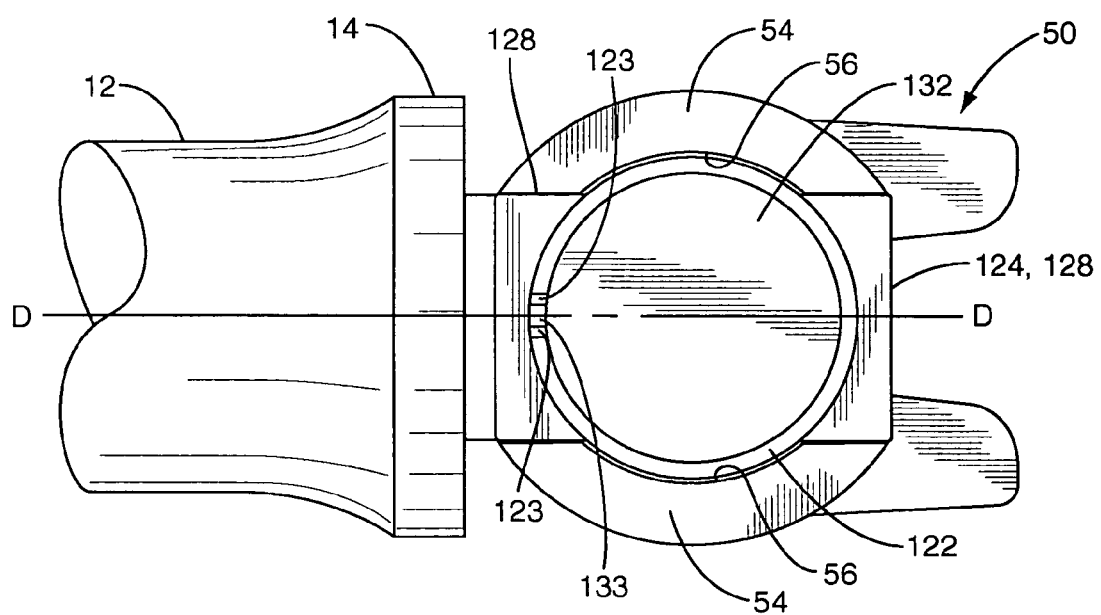
FIG. 9 is a top view of a retainer of an insertion tool and an attached implant device according to one embodiment.

FIG. 8 also shows that the biasing member 122 is marginally wider than the retaining walls 128 of the retainer body 124. FIG. 9 illustrates that this configuration mates with a corresponding configuration in a hook 50. Specifically, the biasing member 122 in the present embodiment engages the threaded portion 56 of the sidewalls 54 of hook 50. FIG. 9 also shows that upon inserting the retainer 120 into the hook 50, the biasing member 122 compresses slightly, creating a reaction force that frictionally engages the hook 50. The compression of the biasing member 122 is visible in the vicinity of the orienting feature 133, where the amount of gap 123 on either side of the orienting feature 133 is reduced as compared to FIG. 8.

Figure 10:
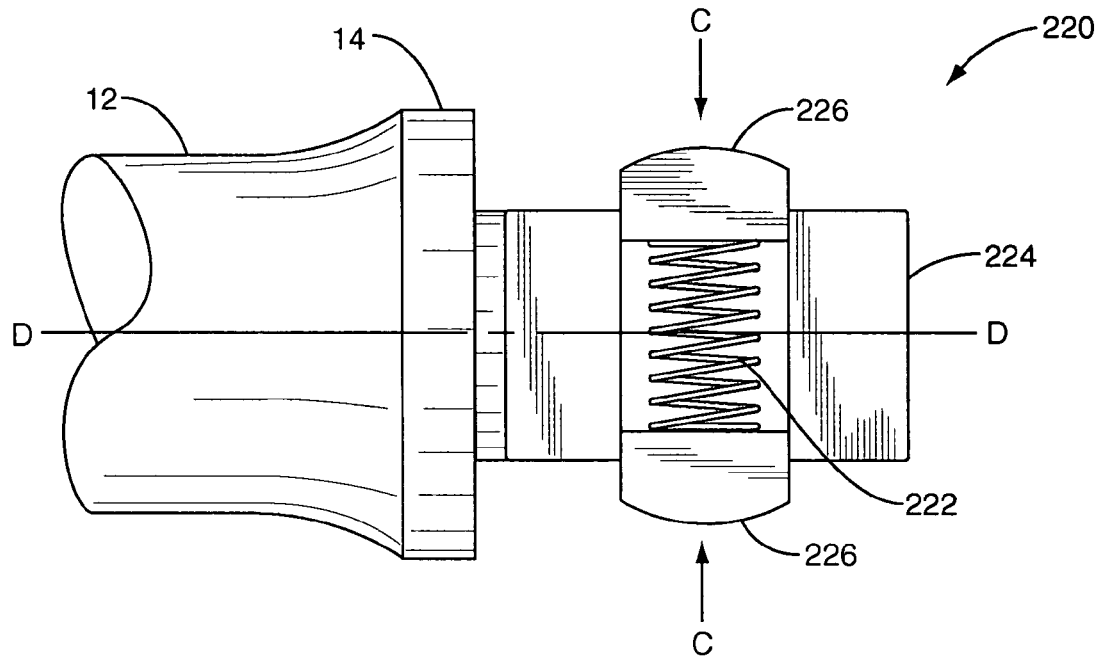
FIG. 10 is a top view of a retainer of an insertion tool according to one embodiment.
Figure 11:
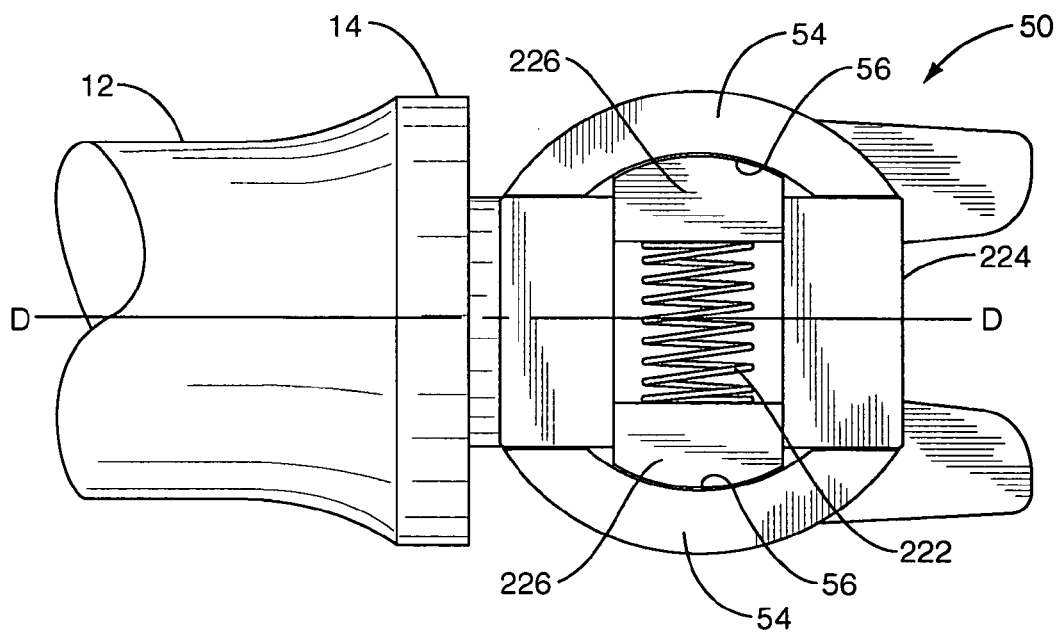
FIG. 11 is a top view of a retainer of an insertion tool and an attached implant device according to one embodiment.

In yet another embodiment of a retainer 220 illustrated in FIGS. 10 and 11, a biasing member 222 is used to apply a frictional retaining force when compressed in the direction of arrows C. A single biasing member 222 is illustrated though a plurality may be used. However, in contrast with previously described embodiments, the biasing member 222 in this embodiment does not directly contact a hook 50 of the type shown in the various Figures. Instead, the biasing member 222 imparts a reactive force on complementary plungers 226 disposed within a head 224 and that are configured to fit within the threaded portion 56 of the sidewalls 54 of hook 50. FIG. 11 shows this same embodiment with the hook 50 attached to the retainer 220 and the plungers 226 compressed as compared to the position shown in FIG. 10.

As with the embodiment of the retainer 20 shown in FIGS. 1-2, and 4-5, the retention mechanism created by biasing members 122 and 222 provides some flexibility in attaching a hook 50. That is, the adjustability represented by the arrows labeled H in FIG. 3B is equally applicable to these embodiments of the retainer 120, 220. Accordingly, the hook 50 may be rotated slightly up and down in the X-Z plane as indicated by the arrows H relative to the insertion tool 10. This additional degree of flexibility may further improve approach angles during surgical installation as well as in removing the insertion tool 10 from the hook 50.

Figure 12:
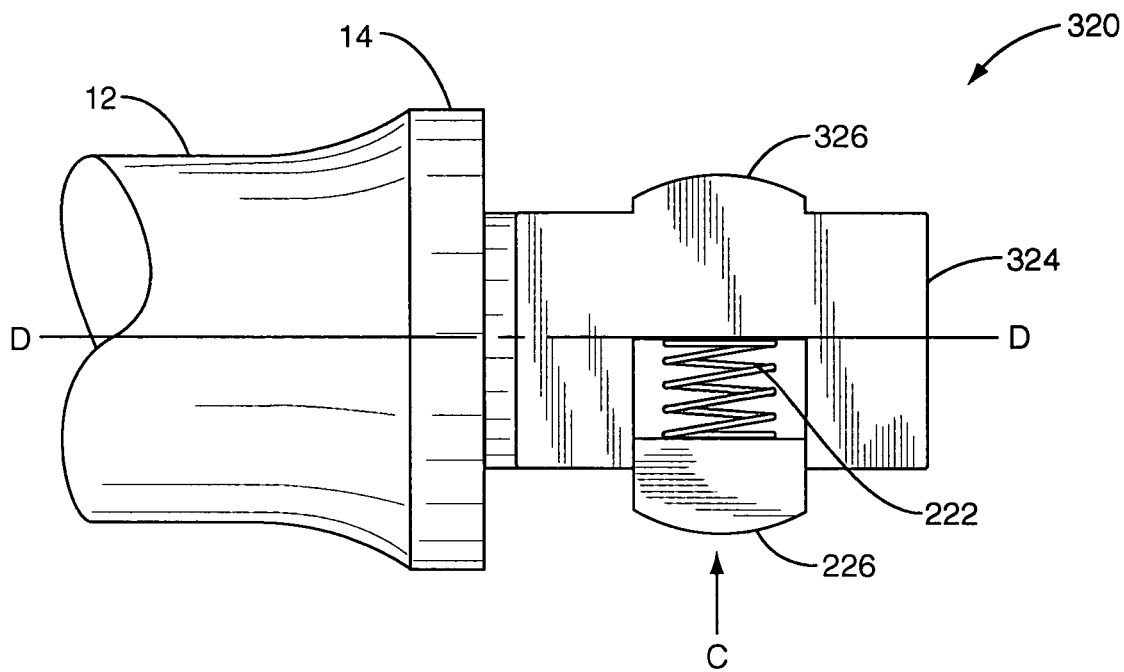
FIG. 12 is a top view of a retainer of an insertion tool according to one embodiment.
Figure 13:
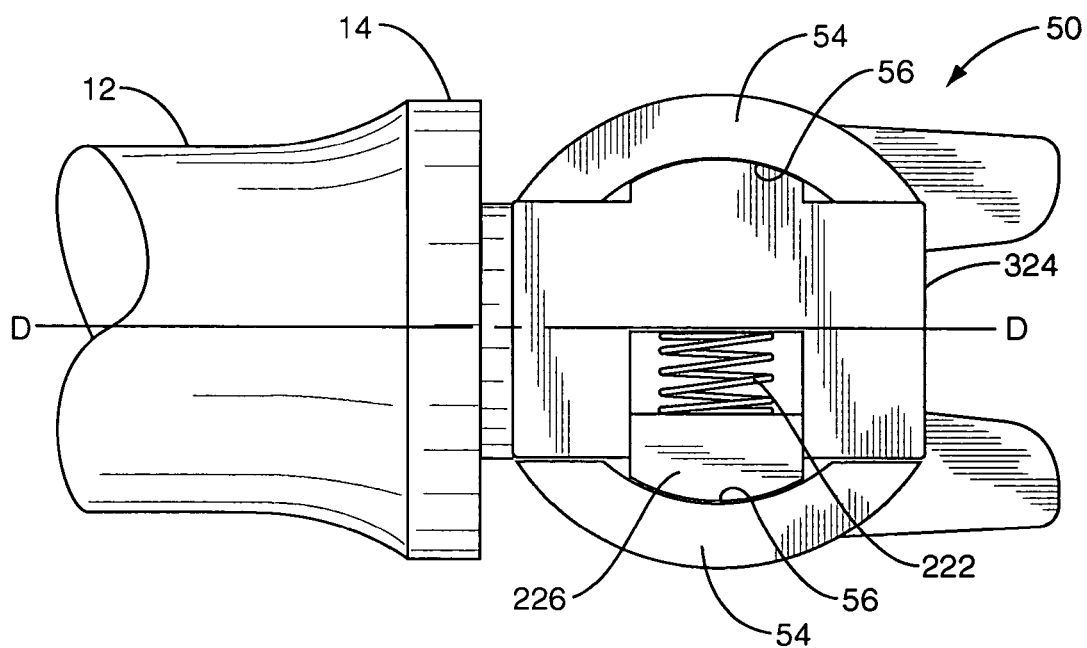
FIG. 13 is a top view of a retainer of an insertion tool and an attached implant device according to one embodiment.

In another embodiment of a retainer 320 illustrated in FIGS. 12 and 13, a biasing member 222 similar to that shown in FIGS. 10 and 11 is used to apply a frictional retaining force when compressed in the direction of arrow C. A single biasing member 222 is illustrated though a plurality may be used. In contrast with the embodiment shown in FIGS. 10 and 11, the biasing member 222 imparts a reactive force on a single plunger 226 that is disposed within a head 324 and is also configured to fit within the threaded portion 56 of sidewalls 54 of hook 50. FIG. 12 shows this same embodiment with the hook 50 attached to the retainer 320 and the single plunger 226 compressed as compared to the position shown in FIG. 12.

The present invention may be carried out in other specific ways than those herein set forth without departing from the scope and essential characteristics of the invention. For example, while certain embodiments described above have contemplated engaging a threaded portion 56 on the interior of the sidewall 54 of hook 50, other hooks may have threaded portions on the exterior of the sidewall 54 or transversely formed through the sidewalls 54. However, the friction forces applied by the various biasing members 22, 122, 222 may be generally applied to the inner surface 58 of the sidewalls 54, regardless of the positioning or existence of threads.

Furthermore, while a hook 50 has been used as an exemplary implant that may be placed with the insertion tool 10, other implant devices may be positioned using the insertion tool. For instance, pedicle screws, clamps for securing a rod to a plate, and other items featuring a rod clamp similar to the illustrated saddle 52 of hook 50 may be inserted and positioned using the insertion tool 10 disclosed herein. The present embodiments are, therefore, to be considered in all respects as illustrative and not restrictive, and all changes coming within the meaning and equivalency range of the appended claims are intended to be embraced therein.

Spatially relative terms such as "under", "below", "lower", "over", "upper", "distal", "proximal", and the like, are used for ease of description to explain the positioning of one element relative to a second element. Further, the terms "down", "downward", "up", "upward", and the like, are used to explain the positioning of the elements as viewed in the Figures. These terms are intended to encompass different orientations of the device in addition to different orientations than those depicted in the figures. Further, terms such as "first", "second", and the like, are also used to describe various elements, regions, sections, etc and are also not intended to be limiting.

What is claimed is:

1. A device to insert a vertebral implant into a patient, the device comprising:
    an elongated handle having a distal end and a proximal end;
    a head attached to the distal end, the head having a longitudinal axis that extends through an inner side of the head that faces towards the handle and an outer side that faces away from the handle; and
    an engagement element operatively connected to the head and movable between an engaged position and a released position, the engagement element disposed in closer proximity to the longitudinal axis in the engaged position than in the released position, the engagement element biased towards the released position; the head including a cross-sectional shape perpendicular to the longitudinal axis that is generally U-shaped with opposing first and second sides and an arcuate bottom; the engagement element includes first and second pairs of opposing cantilevered leaf springs spaced apart along the longitudinal axis of the head with each of the pairs including a first member at the first side of the head and a second member at the second side of the head.

2. The device of claim 1 wherein the engagement element is a compression ring.

3. The device of claim 2 wherein the compression ring comprises a slot that is aligned with an orienting feature on the head.

4. The device of claim 1 wherein the engagement element is biased by a resilient biasing member.

5. The device of claim 1 wherein the engagement element moves between the engaged and released positions in a direction that is substantially lateral to the handle.

6. The device of claim 1 further comprising an enlarged flange disposed adjacent to the head.

7. A device to insert a vertebral implant into a patient, the device comprising:
    an elongated handle having a longitudinal axis and a distal end and a proximal end; and
    a retainer attached to the distal end of the elongated handle, the retainer including a head and a biasing member that are laterally offset from the longitudinal axis of the elongated handle, the head including an enlarged first region and a first wing that extends outward in a first direction from the first region and a second wing that extends outward in a second opposite direction from the first region, the head including a longitudinal axis that extends through the first region and the first and second wings, a width of the first region measured perpendicular to the longitudinal axis of the head being larger than widths of the first and second wings, the biasing member including members on opposing sides of the longitudinal axis of the head, the biasing member being movable between a free configuration with a first width measured perpendicular to the longitudinal axis of the head and an engaged configuration with a second width that is smaller than the first width, the biasing member biased towards the free configuration.

8. The device of claim 7 wherein the retainer further comprises a compression ring that is elastically compressible between the free configuration and the engaged configuration.

9. The device of claim 8 wherein the compression ring comprises a slot that is aligned with an orienting feature on the retainer.

10. The device of claim 7 wherein the retainer further comprises an engagement element that is movable between the free configuration and the engaged configuration and further biased towards the free configuration by a resilient biasing member.

11. The device of claim 7 wherein the retainer further comprises a length measured along the longitudinal axis of the head, the length being the same in the engaged and free configurations.

12. A device to insert a vertebral implant into a patient, the device comprising:
   an elongated handle having a distal end and a proximal end;
   a head attached to the distal end, the head including a cross-sectional shape cut perpendicular to a longitudinal axis of the head that includes a top side, substantially flat opposing lateral sides, and a curved bottom side, the longitudinal axis extending through an inner side of the head that faces towards the handle and an opposing outer side that faces away from the handle; and
   first and second pairs of outwardly biased engagement members operatively connected to the head and inwardly movable from a free configuration to an engaged configuration, each of the first and second pairs including arms positioned on opposing sides of the longitudinal axis of the head, the first and second pairs spaced apart from each other along the longitudinal axis of the head;
   the longitudinal axis of the head is oriented at a transverse angle relative to a longitudinal axis of the handle.

13. The device of claim 12 wherein the outwardly biased engagement element is a compression ring.

14. The device of claim 13 wherein the compression ring comprises a slot that is aligned with an orienting feature on the head.

15. The device of claim 12 wherein each of the arms of the outwardly biased engagement members is a cantilevered spring element.

16. The device of claim 12 wherein the outwardly biased engagement element is biased by a resilient biasing member.

17. The device of claim 12 wherein moving the outwardly biased engagement members from the free configuration to the engaged configuration induces an outwardly directed engagement force.

18. A device to insert a vertebral implant into a patient, the device comprising:
   an elongated handle having a distal end and a proximal end;
   a head attached to the distal end and including an enlarged central region with a first lateral width and opposing first and second wings that extend outward from opposing longitudinal sides of the head and include a smaller second lateral width; and
   an outwardly biased engagement member operatively connected to the head and inwardly movable towards a longitudinal axis of the head from a free configuration to an engaged configuration, the engagement member including first and second arms positioned on opposing lateral sides of the first wing and third and fourth arms positioned on opposing lateral sides of the second wing.

19. The device of claim 18 wherein the first wing extends outward from the head towards the handle.

20. The device of claim 18 wherein lateral sides of the head each include a curved shape.

21. The device of claim 18 further comprising a flange positioned between the head and the handle, the flange including a greater lateral width than the head.

22. The device of claim 18 wherein the first and second wings are identical.

23. A device to insert a vertebral implant into a patient, the device comprising:
   an elongated handle having a distal end and a proximal end;
   a head attached to the distal end, the head having a longitudinal axis with a central section and opposing first and second wings each centered along the longitudinal axis, the central section including a greater lateral width than each of the opposing first and second wings; and
   an engagement element operatively connected to the head and including first and second sets of opposing arms with the first set aligned with the first wing and the second set aligned with the second wing, the engagement member movable between an engaged position with the first and second sets of arms positioned in proximity to the first and second wings respectively and a released position with the first and second set of arms positioned away from the first and second wings respectively, the engagement element biased towards the released position.

* * * * *